US011992709B2

(12) United States Patent
Xu et al.

(10) Patent No.: US 11,992,709 B2
(45) Date of Patent: May 28, 2024

(54) ARRAY-TYPE ULTRASOUND THERAPY SYSTEM

(71) Applicant: Zhejiang University, Zhejiang (CN)

(72) Inventors: Jian Xu, Zhejiang (CN); Yinfei Zheng, Zhejiang (CN)

(73) Assignee: ZHEJIANG UNIVERSITY, Zhejiang (CN)

(*) Notice: Subject to any disclaimer, the term of this patent is extended or adjusted under 35 U.S.C. 154(b) by 10 days.

(21) Appl. No.: 18/074,760

(22) Filed: Dec. 5, 2022

(65) Prior Publication Data

US 2023/0114814 A1 Apr. 13, 2023

Related U.S. Application Data

(63) Continuation of application No. PCT/CN2020/116179, filed on Sep. 18, 2020.

(30) Foreign Application Priority Data

Jun. 10, 2020 (CN) .......................... 202010522960.X

(51) Int. Cl.
A61N 7/00 (2006.01)

(52) U.S. Cl.
CPC ........ A61N 7/00 (2013.01); A61N 2007/0078 (2013.01); A61N 2007/0082 (2013.01)

(58) Field of Classification Search
CPC .................... A61N 7/00; A61N 2007/0078
See application file for complete search history.

(56) References Cited

U.S. PATENT DOCUMENTS

| 2002/0151777 | A1  | 10/2002 | Hynynen et al. |
| 2006/0287596 | A1* | 12/2006 | Johnson ............... A61B 8/0825 600/437 |
| 2008/0243004 | A1* | 10/2008 | Seto ..................... A61B 8/4438 600/459 |
| 2018/0193675 | A1  | 7/2018  | Vortman et al. |

FOREIGN PATENT DOCUMENTS

| CN | 104826243 A | 8/2015 |
| CN | 108144199 A | 6/2018 |
| CN | 110177599 A | 8/2019 |
| CN | 111589001 A | 8/2020 |

OTHER PUBLICATIONS

International Search Report and Written Opinion dated Mar. 10, 2021 in corresponding PCT application No. PCT/CN2020/116179.

* cited by examiner

Primary Examiner — Hien N Nguyen
(74) Attorney, Agent, or Firm — NIELDS, LEMACK & FRAME, LLC

(57) ABSTRACT

The present disclosure discloses an array-type ultrasound therapy system. The ultrasound therapy system includes an ultrasound therapy control unit, an ultrasound transducer driving array, and an ultrasound transducer array. The ultrasound transducer array includes n ultrasound transducers; and a detection signal output end of the ultrasound transducer configured to detect ultrasound echoes generated during ultrasound therapy is connected to a feedback signal input end of the ultrasound therapy control unit. A control signal output end of the ultrasound therapy control unit is connected to an input end of the ultrasound transducer driving array, and an output end of the ultrasound transducer driving array is connected to a driving end of each of the ultrasound transducers configured to perform the ultrasound therapy.

9 Claims, 5 Drawing Sheets

1

ARRAY-TYPE ULTRASOUND THERAPY SYSTEM

CROSS REFERENCE TO RELATED APPLICATION

The present application is a continuation of PCT/CN2020/116179 filed Sep. 18, 2020 and claims the priority of Chinese Patent Application No. 202010522960.X, filed with the China National Intellectual Property Administration (CNIPA) on Jun. 10, 2020, and entitled "ARRAY-TYPE ULTRASOUND THERAPY SYSTEM", the disclosures of which are incorporated herein by reference in their entireties.

TECHNICAL FIELD

The present disclosure relates to the technical field of ultrasound therapy, and in particular to an array-type ultrasound therapy system.

BACKGROUND ART

Low-intensity ultrasound has attracted wide attention due to its biological effect, and biological effect-based ultrasound physiotherapy instruments have been widely used in clinical practice. Scientists discovered in 1978 for the first time that low-intensity focused ultrasound can stimulate the amplitude and frequency of uterine contractions in mice. The accelerated uterine contractions have a function of hemostasis. However, postpartum hemorrhage has always been the number one killer of maternal death in clinical practice. Since ultrasound instruments are universal, different protocols can be compiled according to actual therapy needs. However, there are few instruments special for postpartum uterine involution. The existing ultrasound instruments special for postpartum uterine therapy are not only bulky, but also have complicated operation, poor configurability and low therapeutic efficiency, and only support a dynamic therapy mode. Moreover, the ultrasound instruments for postpartum uterine therapy require medical staff to constantly move a probe to prevent from generating therapeutic hot spots. Therefore, achieving static therapy with the low-intensity ultrasound is very important to improve the therapeutic efficiency and enhance the therapeutic experience for patients and medical staff. How to achieve the static therapy with the low-intensity ultrasound has become a technical problem to be solved urgently.

SUMMARY

An objective of the present disclosure is to provide an array-type ultrasound therapy system to achieve low-intensity static ultrasound therapy.

To achieve the above objective, the present disclosure provides the following solutions:

An array-type ultrasound therapy system includes an ultrasound therapy control unit, an ultrasound transducer driving array, and an ultrasound transducer array; the ultrasound transducer array includes n ultrasound transducers, where n−1 of the n ultrasound transducers are configured to perform ultrasound therapy, and the remaining one ultrasound transducer is configured to detect ultrasound echoes generated during the ultrasound therapy;

a detection signal output end of the ultrasound transducer configured to detect the ultrasound echoes generated during the ultrasound therapy is connected to a feedback signal input end of the ultrasound therapy control unit;

a control signal output end of the ultrasound therapy control unit is connected to an input end of the ultrasound transducer driving array, and an output end of the ultrasound transducer driving array is connected to a driving end of each of the ultrasound transducers configured to perform the ultrasound therapy; and the ultrasound therapy control unit is configured to predict a probability of hot spot generation in an ultrasound therapy process according to the ultrasound echoes and adjust an amplitude or timing of a phased digital signal according to the probability of hot spot generation so as to adjust an intensity of therapeutic sound or a deflectable focusing point of the ultrasound transducer array.

Optionally, the ultrasound transducer driving array includes a digital-to-analog converter (DAC) array, a low-pass filter array, a radio-frequency power amplifier array, and an impedance matching network;

a plurality of control signal output ends of the ultrasound therapy control unit are respectively connected to input ends of a plurality of DACs of the DAC array in one-to-one correspondence;

output ends of the plurality of DACs of the DAC array are respectively connected to input ends of a plurality of low-pass filters of the low-pass filter array in one-to-one correspondence;

output ends of the plurality of low-pass filters of the low-pass filter array are respectively connected to input ends of a plurality of radio-frequency power amplifiers of the radio-frequency power amplifier array in one-to-one correspondence;

output ends of the plurality of radio-frequency power amplifiers of the radio-frequency power amplifier array are respectively connected to input ends of a plurality of impedance matchers of the impedance matching network in one-to-one correspondence; and output ends of the plurality of impedance matchers of the impedance matching network are respectively connected to the driving ends of the n−1 ultrasound transducers configured to perform the ultrasound therapy of the ultrasound transducer array in one-to-one correspondence.

Optionally, the ultrasound therapy system further includes an amplifier and an analog-to-digital converter (ADC);

the amplifier and the ADC are arranged between the ultrasound transducer configured to detect the ultrasound echoes generated during the ultrasound therapy and the ultrasound therapy control unit; and the detection signal output end of the ultrasound transducer configured to detect the ultrasound echoes generated during the ultrasound therapy is connected to an input end of the amplifier, an output end of the amplifier is connected to an input end of the ADC, and an output end of the ADC is connected to the feedback signal input end of the ultrasound therapy control unit.

Optionally, the ultrasound transducer array is a linear phased array, a rectangular phased array, or a circular phased array.

Optionally, the ultrasound transducer array operates in a single-array element operating mode, a single-row array element operating mode, or a dynamic deflectable-focusing scan operating mode.

Optionally, the ultrasound therapy control unit includes a field-programmable gate array (FPGA) unit, a key unit, and a display unit;

both the key unit and the display unit are connected to the FPGA unit; and the FPGA unit is separately connected to the detection signal output end of the ultrasound transducer configured to detect the ultrasound echoes generated during the ultrasound therapy and the input end of the ultrasound transducer driving array.

Optionally, the FPGA unit includes a scan cycle timer and a plurality of phased digital signal generation modules arranged in parallel, and the plurality of phased digital signal generation modules are respectively connected to the plurality of DACs of the DAC array of the ultrasound transducer driving array in one-to-one correspondence;

each of the phased digital signal generation modules includes a delay parameter register, a first delay counter, an address parameter register, a first comparator, an address generator, a second delay counter, a second comparator, and a phased digital signal generator; the delay parameter register stores a coarse-adjustment-level delay parameter and a fine-adjustment-level delay parameter; and the address parameter register stores an access address of the coarse-adjustment-level delay parameter and an access address of the fine-adjustment-level delay parameter;

an output end of the scan cycle timer is separately connected to an enabling end of the first delay counter and a first enabling end of the address generator, an output end of the address generator is connected to a control end of the address parameter register, an output end of the address parameter register is connected to a control end of the delay parameter register, and a coarse-adjustment-level delay parameter output end of the delay parameter register is connected to a first input end of the first comparator;

an output end of the first delay counter is connected to a second input end of the first comparator; an output end of the first comparator is connected to a second enabling end of the address generator; and a fine-adjustment-level delay parameter output end of the delay parameter register is connected to a first input end of the second comparator;

an output end of the first comparator is connected to an enabling end of the second delay counter; an output end of the second delay counter is connected to a second input end of the second comparator; and an output end of the second comparator is connected to an enabling end of the phased digital signal generator, and an output end of the phased digital signal generator is connected to an input end of the ultrasound transducer driving array.

Optionally, the FPGA unit further includes an ultrasound echo signal processor, a cavitation determination device, and a delay parameter updating module;

an input end of the ultrasound echo signal processor is connected to the detection signal output end of the ultrasound transducer configured to detect the ultrasound echoes generated during the ultrasound therapy;

an output end of the ultrasound echo signal processor is separately connected to an input end of the cavitation determination device and an input end of the delay parameter updating module;

an output end of the delay parameter updating module is connected to an input end of the delay parameter register; and an output end of the cavitation determination device is connected to an enabling end of the delay parameter updating module; and the cavitation determination device is configured to determine whether a harmonic signal is present in the ultrasound echoes processed by the ultrasound echo signal processor and determine a cavitation probability according to a type of the harmonic signal, and when the cavitation probability is greater than a probability threshold, the delay parameter updating module is enabled to generate updated delay parameters according to the ultrasound echoes processed by the ultrasound echo signal processor and store the updated delay parameters into the delay parameter register.

Optionally, the FPGA unit further includes an amplitude adjustment module;

the amplitude adjustment module includes an enabling end connected to the output end of the cavitation determination device and an input end connected to the output end of the ultrasound echo signal processor; and an output end of the amplitude adjustment module is connected to an input end of the phased digital signal generator.

Optionally, the FPGA unit further includes a liquid-crystal display (LCD) controller module; and the LCD controller module is connected to the display unit.

According to the specific embodiments provided by the present disclosure, the present disclosure provides the following technical effects:

The present disclosure discloses an array-type ultrasound therapy system, where the ultrasound therapy system includes an ultrasound therapy control unit, an ultrasound transducer driving array, and an ultrasound transducer array; the ultrasound transducer array includes n ultrasound transducers, where n−1 of the n ultrasound transducers are configured to perform ultrasound therapy, and the remaining one ultrasound transducer is configured to detect ultrasound echoes generated during the ultrasound therapy; a detection signal output end of the ultrasound transducer configured to detect the ultrasound echoes generated during the ultrasound therapy is connected to a feedback signal input end of the ultrasound therapy control unit; a control signal output end of the ultrasound therapy control unit is connected to an input end of the ultrasound transducer driving array, and an output end of the ultrasound transducer driving array is connected to a driving end of each of the ultrasound transducers configured to perform the ultrasound therapy; and the ultrasound therapy control unit is configured to predict a probability of hot spot generation in an ultrasound therapy process according to the ultrasound echoes and adjust an amplitude or timing of a phased digital signal according to the probability of hot spot generation so as to adjust an intensity of therapeutic sound or a deflectable focusing point of the ultrasound transducer array. According to the present disclosure, the ultrasound transducer configured to detect the ultrasound echoes generated during the ultrasound therapy monitors a therapy region, and upon determining that the probability of hot spot generation is great, the ultrasound therapy control unit adjusts the intensity of therapeutic sound and the deflectable focusing point of the ultrasound transducer array to achieve low-intensity static ultrasound therapy.

BRIEF DESCRIPTION OF THE DRAWINGS

To describe the technical solutions in the embodiments of the present disclosure or in the prior art more clearly, the accompanying drawings required in the embodiments are briefly described below. Apparently, the accompanying drawings in the following descriptions show merely some embodiments of the present disclosure, and a person of ordinary skill in the art may still derive other accompanying drawings from these accompanying drawings without creative efforts.

DETAILED DESCRIPTION OF THE EMBODIMENTS

The technical solutions in the embodiments of the present disclosure are clearly and completely described below with reference to the accompanying drawings in the embodiments of the present disclosure. Apparently, the described embodiments are merely some rather than all of the embodiments of the present disclosure. On the basis of the embodiments of the present disclosure, all other embodiments derived by a person of ordinary skill in the art, without involving any creative effort, fall within the scope of protection of the present disclosure.

An objective of the present disclosure is to provide an array-type ultrasound therapy system to achieve low-intensity static ultrasound therapy.

To make the objective, features, and advantages of the present disclosure clearer and more comprehensible, the present disclosure is further described in detail below in combination with the accompanying drawings and specific implementations.

According to the present disclosure, an ultrasound phased array technology is used, and each array element can be independently controlled. Ultrasound transducers have a detection function for monitoring the generation of cavitation, an extreme value of sound intensity is estimated by using correspondence between a cavitation threshold and a sound pressure, and a large sound intensity often leads to the generation of tissue hot spots.

The system of the present disclosure can achieve low-intensity static ultrasound therapy. The ultrasound therapy system does not require to perform therapy by moving, greatly reduces the probability of hot spot generation, has relatively uniform distribution of sound field and high configurability of a therapy protocol, operates safely and stably, can be widely used in fields related to low-intensity gynecological ultrasound therapy and rehabilitation, and provides a static, convenient and automatic system platform for clinical application of low-intensity ultrasound therapy. Moreover, the introduction of ultrasound detection technology can monitor the generation of hot spots, and feed back to a generation unit to dynamically adjust an emitted beam, thereby reducing a probability of forming the hot spots by interference from an ultrasound beam.

The system of the present disclosure can provide a static therapy mode and can monitor cavitation phenomenon in a therapy region by the detection technology of the ultrasound transducers to estimate the probability of hot spot generation, cavitation information monitored by the ultrasound transducers is fed back to an ultrasound therapy control unit, and the ultrasound therapy control unit dynamically adjusts a therapy solution according to the feedback information. The ultrasound therapy system provides a static ultrasound therapy solution that is simple to operate, has a high degree of digitization, a friendly human-computer interaction interface and good controllability of ultrasound dose, and is safe and reliable.

Figure 1:
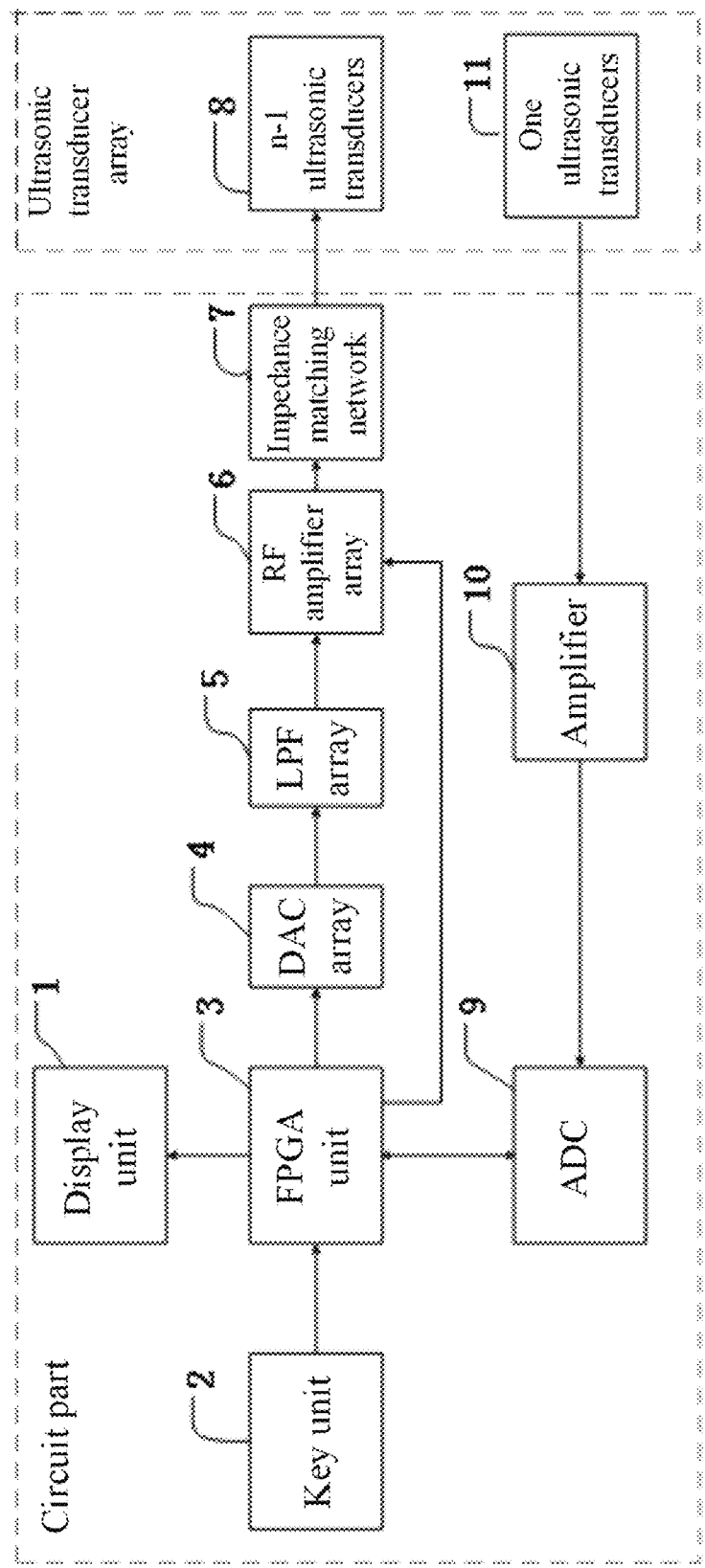
FIG. 1 is a structural diagram of an array-type ultrasound therapy system provided by the present disclosure.

The objective of the present disclosure is achieved by means of the following technical solutions: as shown in FIG. 1, the ultrasound therapy system includes an ultrasound therapy control unit, an ultrasound transducer driving array, and an ultrasound transducer array. The ultrasound transducer array includes n ultrasound transducers, where n−1 of the n ultrasound transducers 8 are configured to perform ultrasound therapy, and the remaining one ultrasound transducer 11 is configured to detect ultrasound echoes generated during the ultrasound therapy. A detection signal output end of the ultrasound transducer 11 configured to detect the ultrasound echoes generated during the ultrasound therapy is connected to a feedback signal input end of the ultrasound therapy control unit; a control signal output end of the ultrasound therapy control unit is connected to an input end of the ultrasound transducer driving array, and an output end of the ultrasound transducer driving array is connected to a driving end of each of the ultrasound transducers 8 configured to perform the ultrasound therapy. The ultrasound therapy control unit is configured to predict a probability of hot spot generation in an ultrasound therapy process according to the ultrasound echoes and adjust an amplitude or timing of a phased digital signal according to the probability of hot spot generation so as to adjust an intensity of therapeutic sound or a deflectable focusing point of the ultrasound transducer array.

As shown in FIG. 1, the ultrasound transducer driving array includes a digital-to-analog converter (DAC) array 4, a low-pass filter array (corresponding to a low-pass filter (LPF) array 5 in FIG. 1), a radio-frequency power amplifier array (corresponding to a radio-frequency (RF) amplifier array 6 in FIG. 1), and an impedance matching network 7. A plurality of control signal output ends of the ultrasound therapy control unit are respectively connected to input ends of a plurality of DACs of the DAC array 4 in one-to-one correspondence; output ends of the plurality of DACs of the DAC array 4 are respectively connected to input ends of a plurality of low-pass filters of the low-pass filter array in one-to-one correspondence; output ends of the plurality of low-pass filters of the low-pass filter array are respectively connected to input ends of a plurality of radio-frequency power amplifiers of the radio-frequency power amplifier array in one-to-one correspondence; output ends of the plurality of radio-frequency power amplifiers of the radio-frequency power amplifier array are respectively connected to input ends of a plurality of impedance matchers of the impedance matching network 7 in one-to-one correspondence; and output ends of the plurality of impedance matchers of the impedance matching network 7 are respectively connected to the driving ends of the n−1 ultrasound transducers 8 configured to perform the ultrasound therapy of the ultrasound transducer array in one-to-one correspondence.

As shown in FIG. 1, the ultrasound therapy system further includes an amplifier 10 and an analog-to-digital converter (ADC) 9. The amplifier 10 and the ADC 9 are arranged between the ultrasound transducer 11 configured to detect the ultrasound echoes generated during the ultrasound therapy and the ultrasound therapy control unit. The detection signal output end of the ultrasound transducer 11 configured to detect the ultrasound echoes generated during the ultrasound therapy is connected to an input end of the amplifier 10, an output end of the amplifier 10 is connected to an input end of the ADC 9, and an output end of the ADC 9 is connected to the feedback signal input end of the ultrasound therapy control unit.

As shown in FIG. 1, the ultrasound therapy control unit includes a field-programmable gate array (FPGA) unit 3, a key unit 2, and a display unit 1. Both the key unit and the display unit are connected to the FPGA unit; and the FPGA unit is separately connected to the detection signal output end of the ultrasound transducer configured to detect the ultrasound echoes generated during the ultrasound therapy and the input end of the ultrasound transducer driving array.

Figure 2:
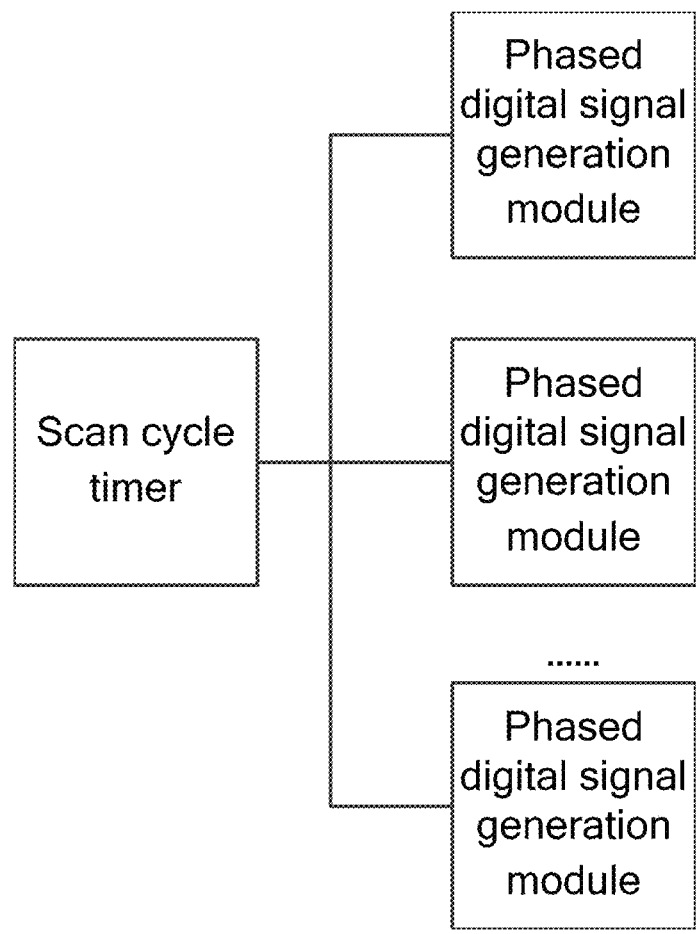
FIG. 2 is a structural composition diagram of a field-programmable gate array (FPGA) unit provided by the present disclosure.

As shown in FIG. 2, the FPGA unit includes a scan cycle timer and a plurality of phased digital signal generation modules arranged in parallel. The plurality of phased digital signal generation modules are respectively connected to the plurality of DACs of the DAC array of the ultrasound transducer driving array in one-to-one correspondence.

Figure 3:
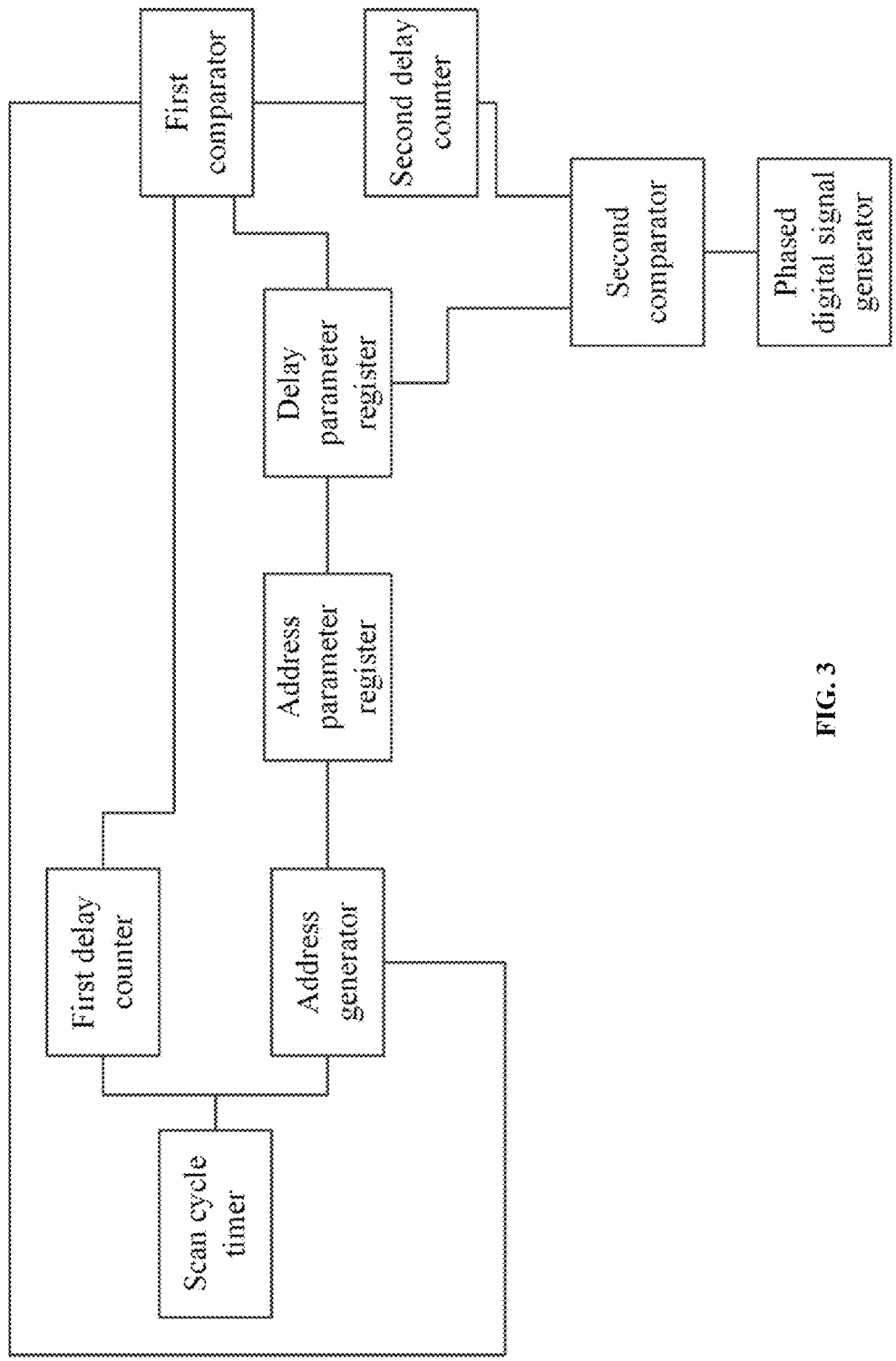
FIG. 3 is a structural composition diagram of a phased digital signal generation module provided by the present disclosure.

As shown in FIG. 3, each of the phased digital signal generation modules includes a delay parameter register, a first delay counter, an address parameter register, a first comparator, an address generator, a second delay counter, a second comparator, and a phased digital signal generator. The delay parameter register stores a coarse-adjustment-level delay parameter and a fine-adjustment-level delay parameter. The address parameter register stores an access address of the coarse-adjustment-level delay parameter and an access address of the fine-adjustment-level delay parameter. An output end of the scan cycle timer is separately connected to an enabling end of the first delay counter and a first enabling end of the address generator, an output end of the address generator is connected to a control end of the address parameter register, an output end of the address parameter register is connected to a control end of the delay parameter register, and a coarse-adjustment-level delay parameter output end of the delay parameter register is connected to a first input end of the first comparator. An output end of the first delay counter is connected to a second input end of the first comparator; an output end of the first comparator is connected to a second enabling end of the address generator; and a fine-adjustment-level delay parameter output end of the delay parameter register is connected to a first input end of the second comparator. An output end of the first comparator is connected to an enabling end of the second delay counter; an output end of the second delay counter is connected to a second input end of the second comparator; and an output end of the second comparator is connected to an enabling end of the phased digital signal generator, and an output end of the phased digital signal generator is connected to an input end of the ultrasound transducer driving array.

The FPGA unit further includes an ultrasound echo signal processor, a cavitation determination device, and a delay parameter updating module. An input end of the ultrasound echo signal processor is connected to the detection signal output end of the ultrasound transducer configured to detect the ultrasound echoes generated during the ultrasound therapy; an output end of the ultrasound echo signal processor is separately connected to an input end of the cavitation determination device and an input end of the delay parameter updating module; an output end of the delay parameter updating module is connected to an input end of the delay parameter register; and an output end of the cavitation determination device is connected to an enabling end of the delay parameter updating module. The cavitation determination device is configured to determine whether a harmonic signal is present in the ultrasound echoes processed by the ultrasound echo signal processor and determine a cavitation probability according to a type of the harmonic signal, and when the cavitation probability is greater than a probability threshold, the delay parameter updating module is enabled to generate updated delay parameters according to the ultrasound echoes processed by the ultrasound echo signal processor and store the updated delay parameters into the delay parameter register.

The FPGA unit further includes an amplitude adjustment module. The amplitude adjustment module includes an enabling end connected to the output end of the cavitation determination device and an input end connected to the output end of the ultrasound echo signal processor; and an output end of the amplitude adjustment module is connected to an input end of the phased digital signal generator.

Figure 4:
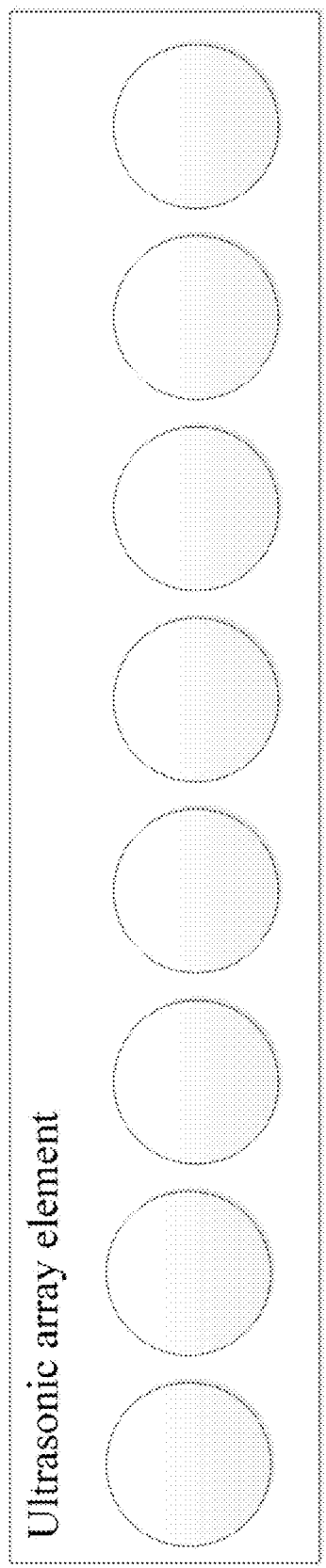
FIG. 4 is a structural schematic diagram of a linear phased array provided by the present disclosure.
Figure 5:
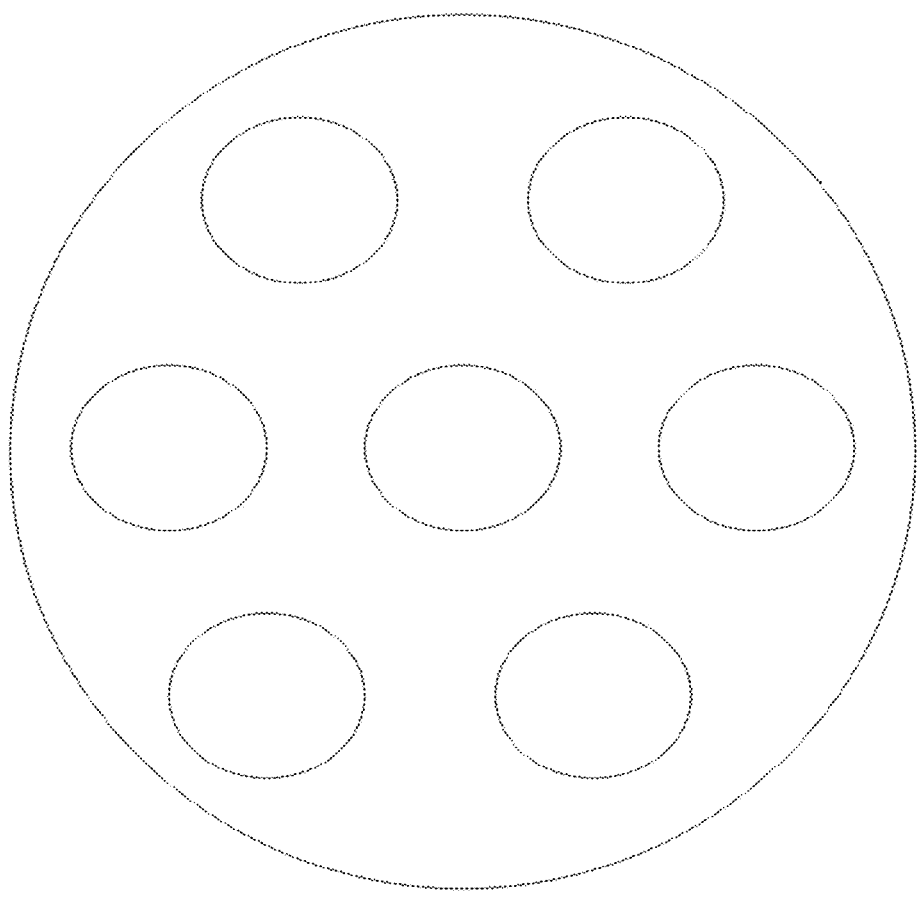
FIG. 5 is a structural schematic diagram of a circular phased array provided by the present disclosure.

The ultrasound transducer array is a linear phased array (as shown in FIG. 4), a rectangular phased array, or a circular phased array (as shown in FIG. 5). The ultrasound transducer array operates in a single-array element operating mode, a single-row array element operating mode, or a dynamic deflectable-focusing scan operating mode.

Specifically, if the ultrasound transducer array is a circular phased array, it may operate in a single-array element operating mode or a dynamic deflectable-focusing scan operating mode; and if the ultrasound transducer array is a linear phased array or a rectangular phased array, it may operate in a single-array element operating mode or a single-row array element operating mode.

If the ultrasound transducer array operates in a dynamic deflectable-focusing scan operating mode, the delay parameter updating module updates the delay parameters in the delay parameter register to adjust the deflectable focusing point of the ultrasound transducer array so as to prevent from generating the hot spots in the therapy process.

If the ultrasound transducer array operates in a single-array element operating mode or a single-row array element operating mode, the amplitude adjustment module adjusts an amplitude of a signal generated by the phased digital signal generator to prevent from generating the hot spots in the therapy process.

The FPGA unit of the present disclosure further includes a liquid-crystal display (LCD) controller module. The LCD controller module is connected to the display unit for driving the display unit to display therapy content.

The operating process of the low-intensity static ultrasound therapy system includes the following steps:

(1) the key unit 2 sets therapy parameters, the FPGA unit 3 selects the amplitude and phase of a waveform internally according to the inputted parameters, the phased digital signal generator outputs a corresponding sinusoidal digital excitation signal, the outputted sinusoidal digital excitation signal is converted into a sinusoidal analog signal by the DAC array, the sinusoidal analog signal enters the low-pass filter array to obtain a smoothed sinusoidal signal, and the smoothed sinusoidal signal drives the ultrasound transducers to operate by the radio-frequency power amplifier array (a RF amplifier array). The ultrasound transducer array herein can be independently triggered. Therefore, when the FPGA unit designs a digital phase delay, each sinusoidal signal is enabled to generate a certain phase difference. The design of an appropriate phase delay implements deflectable focusing scan based on a phased focal point, thereby achieving uniform distribution of an ultrasound field within the entire therapy region.

(2) The ultrasound transducer 11 configured to detect the ultrasound echoes generated during the ultrasound therapy is adjusted to form a certain included angle θ with the ultrasound transducer array 8, so as to be capable of monitoring a focal point region. The ultrasound echoes detected by the ultrasound transducer configured to detect the ultrasound echoes generated during the ultrasound therapy are subjected to acoustoelectric conversion, then are inputted into the amplifier 10 in a form of an electric signal for amplifying, and are inputted into the FPGA unit 3 by the ADC 9.

(3) After the FPGA unit 3 receives the signal inputted by the ADC 9, a target frequency is obtained by the ultrasound echo signal processor (filtered by a digital filter). According to the fact that the entire therapy process is a random stationary process, the target frequency can be used to estimate the probability of hot spot generation. An ultrasound dose and a scan position are then adjusted.

The basic principle of the low-intensity static ultrasound therapy instrument used is described in detail below:

In the process of ultrasound therapy of uterine smooth muscle atony, an ultrasound coupling agent is first evenly applied on the transducer array, then the ultrasound coupling agent is evenly applied to a therapy part of a patient, and finally the ultrasound transducer array of the ultrasound therapy system for the ultrasound therapy is fixed at the therapy part which refers to the abdomen above the uterus. The ultrasound transducer configured to detect the ultrasound echoes generated during the ultrasound therapy intersects the therapy region at a certain inclination angle. The ultrasound therapy system is powered on, the therapy protocol is selected, and the protocol here includes a therapy time, a therapy sound intensity, a therapy area, a scan speed (scan cycle), etc. Upon completing the selection of the therapy protocol, the static ultrasound therapy can be started. Due to reflection and interference, the hot spots may be generated in the therapy region. A peak sound pressure in the hot spot region is high, and the high peak sound pressure is likely to cause cavitation. At a frequency of 1 MHz, a transient sound intensity threshold is about 10 W/cm$^2$. When transient cavitation occurs, second and higher harmonics are generated during the collapse of cavitation bubbles. At this time, only the ultrasound transducer configured to detect the ultrasound echoes generated during the ultrasound therapy requires to monitor the higher harmonics. That is, the transient cavitation is considered to occur. Moreover, the intensity of cavitation is determined according to the intensity of the higher harmonics, and the probability of generating therapeutic hot spots is then estimated. The estimated probability of hot spot generation is fed back to the FPGA unit, and the FPGA unit dynamically adjusts the intensity of therapeutic ultrasound or the deflectable focusing point, thereby preventing from generating the therapeutic hot spots, and achieving low-intensity static ultrasound therapy.

As shown in FIG. 3, the operating principle of the delay phased technology in the present disclosure is as follows: a delay technology device is enabled by means of a control signal (scan cycle, enabled once in each scan cycle), then the coarse-adjustment-level delay parameter is retrieved from the delay parameter register, and both the value of the first delay counter and the coarse-adjustment-level delay parameter are inputted into the first comparator. When the value of the first delay counter is the same as the inputted coarse-adjustment-level delay parameter, the first comparator outputs an enabling signal for enabling the address generator to retrieve the fine-adjustment-level delay parameter from the delay parameter register and enabling the second delay counter to input both the value of the second delay counter and the fine-adjustment-level delay parameter into the second comparator. When the value of the second delay counter is the same as the inputted fine-adjustment-level delay parameter, the phased digital signal generator is enabled to generate a waveform, output same in a form of a digital pulse, and output same in a form of an analog signal after passing through the DAC array and the low-pass filter array. The LCD controller module displays the content of the therapy protocol, such as the therapy time, the therapy sound intensity, the therapy area, and the scan speed on an LCD. This system can perform phased array scan within a range of 60°, and the sound intensity is continuously adjustable within a range of 0-4/cm$^2$.

The beneficial effects of the present disclosure are as follows: according to the present disclosure, the phased array technology is used, and each array element is independently controlled, that is, the emission phase and amplitude of each array element can be adjusted, and a relatively uniform focus sound intensity can be obtained during deflectable focusing scan of the phased array. An operating center frequency of this phased array is 1 M, and at this frequency, its transient cavitation threshold is about 10 W/cm$^2$. Therefore, when the focus sound intensity is higher than the cavitation threshold, the transient cavitation signal can be monitored by the ultrasound transducer configured to detect the ultrasound echoes generated during the ultrasound therapy, and the ultrasound dose, focus movement speed and focus shape are dynamically adjusted according to the monitored transient cavitation information. A scan angle of the phased array can reach 60°, which can scan the therapy region within a larger range. In combination with precise delay characteristics of FPGA, precise deflectable focusing can be achieved. Due to the use of phased array scan and ultrasound detection to monitor acoustic cavitation phenomenon, the probability of hot spot generation is reduced while achieving static therapy, and a safe, convenient and automatic ultrasound therapy platform is provided for the clinic, thereby improving the therapeutic efficiency for medical staff, and improving the therapeutic experience for patients.

Specific examples are used herein to explain the principles and embodiments of the present disclosure. The foregoing description of the embodiments is merely intended to help understand the method of the present disclosure and its core ideas; besides, various modifications may be made by a person of ordinary skill in the art to specific embodiments and the scope of application in accordance with the ideas of the present disclosure. In conclusion, the content of the present description shall not be construed as limitations to the present disclosure.

The above embodiments are provided merely for an objective of describing the present disclosure and are not intended to limit the scope of the present disclosure. The scope of the present disclosure is defined by the appended claims. Various equivalent replacements and modifications made without departing from the spirit and scope of the present disclosure should all fall within the scope of the present disclosure.

What is claimed is:

1. An array-type ultrasound therapy system, wherein the ultrasound therapy system comprises an ultrasound therapy control unit, an ultrasound transducer driving array, and an ultrasound transducer array; the ultrasound therapy control unit is provided with a field programmable gate array (FPGA) unit, which is separately connected to a detection signal output end of an ultrasound transducer configured to detect ultrasound echoes generated during an ultrasound therapy and an input end of the ultrasound transducer driving array, and the FPGA unit is configured to receive therapy parameter that is set manually and output therapy content for displaying on a display unit; the ultrasound transducer array comprises n ultrasound transducers, wherein n−1 of the n ultrasound transducers are configured to perform ultrasound therapy, and remaining one ultrasound transducer is configured to detect ultrasound echoes generated during the ultrasound therapy;

the detection signal output end of the ultrasound transducer configured to detect the ultrasound echoes generated during the ultrasound therapy is connected to a feedback signal input end of the ultrasound therapy control unit;

a control signal output end of the ultrasound therapy control unit is connected to an input end of the ultrasound transducer driving array, and an output end of the ultrasound transducer driving array is connected to a driving end of each of the ultrasound transducers configured to perform the ultrasound therapy; and the ultrasound therapy control unit is configured to predict a probability of hot spot generation in an ultrasound therapy process according to the ultrasound echoes and adjust an amplitude or timing of a phased digital signal according to the probability of hot spot generation so as to adjust an intensity of therapeutic sound or a deflectable focusing point of the ultrasound transducer array.

2. The array-type ultrasound therapy system according to claim 1, wherein the ultrasound transducer driving array comprises a digital-to-analog converter (DAC) array, a low-pass filter array, a radio-frequency power amplifier array, and an impedance matching network;

a plurality of control signal output ends of the ultrasound therapy control unit are respectively connected to input ends of a plurality of DACs of the DAC array in one-to-one correspondence;

output ends of the plurality of DACs of the DAC array are respectively connected to input ends of a plurality of low-pass filters of the low-pass filter array in one-to-one correspondence;

output ends of the plurality of low-pass filters of the low-pass filter array are respectively connected to input ends of a plurality of radio-frequency power amplifiers of the radio-frequency power amplifier array in one-to-one correspondence;

output ends of the plurality of radio-frequency power amplifiers of the radio-frequency power amplifier array are respectively connected to input ends of a plurality of impedance matchers of the impedance matching network in one-to-one correspondence; and output ends of the plurality of impedance matchers of the impedance matching network are respectively connected to driving ends of the n−1 ultrasound transducers configured to perform the ultrasound therapy of the ultrasound transducer array in one-to-one correspondence.

3. The array-type ultrasound therapy system according to claim 1, wherein the array-type ultrasound therapy system further comprises an amplifier and an analog-to-digital converter (ADC);

the amplifier and the ADC are arranged between the ultrasound transducer configured to detect the ultrasound echoes generated during the ultrasound therapy and the ultrasound therapy control unit; and the detection signal output end of the ultrasound transducer configured to detect the ultrasound echoes generated during the ultrasound therapy is connected to an input end of the amplifier, an output end of the amplifier is connected to an input end of the ADC, and an output end of the ADC is connected to the feedback signal input end of the ultrasound therapy control unit.

4. The array-type ultrasound therapy system according to claim 1, wherein the ultrasound transducer array is a linear phased array, a rectangular phased array, or a circular phased array.

5. The array-type ultrasound therapy system according to claim 1, wherein the ultrasound transducer array operates in a single-array element operating mode, a single-row array element operating mode, or a dynamic deflectable-focusing scan operating mode.

6. The array-type ultrasound therapy system according to claim 1, wherein the FPGA unit comprises a scan cycle timer and a plurality of phased digital signal generation modules arranged in parallel, and the plurality of phased digital signal generation modules are respectively connected to the plurality of DACs of the DAC array of the ultrasound transducer driving array in one-to-one correspondence;

each of the phased digital signal generation modules comprises a delay parameter register, a first delay counter, an address parameter register, a first comparator, an address generator, a second delay counter, a second comparator, and a phased digital signal generator; the delay parameter register stores a coarse-adjustment-level delay parameter and a fine-adjustment-level delay parameter; and the address parameter register stores an access address of the coarse-adjustment-level delay parameter and an access address of the fine-adjustment-level delay parameter;

an output end of the scan cycle timer is separately connected to an enabling end of the first delay counter and a first enabling end of the address generator, an output end of the address generator is connected to a control end of the address parameter register, an output end of the address parameter register is connected to a control end of the delay parameter register, and a coarse-adjustment-level delay parameter output end of the delay parameter register is connected to a first input end of the first comparator;

an output end of the first delay counter is connected to a second input end of the first comparator; an output end of the first comparator is connected to a second enabling end of the address generator; and a fine-adjustment-level delay parameter output end of the delay parameter register is connected to a first input end of the second comparator;

a second output end of the first comparator is connected to an enabling end of the second delay counter; an output end of the second delay counter is connected to a second input end of the second comparator; and an output end of the second comparator is connected to an enabling end of the phased digital signal generator, and an output end of the phased digital signal generator is connected to an input end of the ultrasound transducer driving array.

7. The array-type ultrasound therapy system according to claim 6, wherein the FPGA unit further comprises an ultrasound echo signal processor, a cavitation determination device, and a delay parameter updating module;

an input end of the ultrasound echo signal processor is connected to the detection signal output end of the ultrasound transducer configured to detect the ultrasound echoes generated during the ultrasound therapy;

an output end of the ultrasound echo signal processor is separately connected to an input end of the cavitation determination device and an input end of the delay parameter updating module;

an output end of the delay parameter updating module is connected to an input end of the delay parameter register; and an output end of the cavitation determination device is connected to an enabling end of the delay parameter updating module; and the cavitation determination device is configured to determine whether a harmonic signal is present in the ultrasound echoes processed by the ultrasound echo signal processor and determine the probability of hot spot according to a type of the harmonic signal, and when the probability of hot spot is greater than a probability threshold, the delay parameter updating module is enabled to generate updated delay parameters according to the ultrasound echoes processed by the ultrasound echo signal processor and store the updated delay parameters into the delay parameter register.

8. The array-type ultrasound therapy system according to claim 7, wherein the FPGA unit further comprises an amplitude adjustment module;

the amplitude adjustment module comprises an enabling end connected to the output end of the cavitation determination device and an input end connected to the output end of the ultrasound echo signal processor; and an output end of the amplitude adjustment module is connected to an input end of the phased digital signal generator.

9. The array-type ultrasound therapy system according to claim 1, wherein the FPGA unit further comprises a liquid-crystal display (LCD) controller module; and the LCD controller module is connected to the display unit.

* * * * *